United States Patent
Wang

(10) Patent No.: US 11,164,296 B2
(45) Date of Patent: Nov. 2, 2021

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 29 days.

(21) Appl. No.: 16/776,526

(22) Filed: Jan. 30, 2020

(65) Prior Publication Data

US 2020/0175662 A1    Jun. 4, 2020

Related U.S. Application Data

(63) Continuation of application No. PCT/JP2018/020700, filed on May 30, 2018.

(30) Foreign Application Priority Data

Aug. 28, 2017    (JP) .............................. JP2017-163010

(51) Int. Cl.
*A61B 5/00* (2006.01)
*A61B 5/055* (2006.01)
(Continued)

(52) U.S. Cl.
CPC ................ *G06T 5/40* (2013.01); *A61B 5/055* (2013.01); *G06T 5/50* (2013.01); *G06T 7/11* (2017.01);
(Continued)

(58) Field of Classification Search
None
See application file for complete search history.

(56) References Cited

U.S. PATENT DOCUMENTS

| 6,584,216 B1 | 6/2003 | Nyul et al. |
| 2005/0043614 A1* | 2/2005 | Huizenga ................ C23F 11/08 600/427 |

(Continued)

FOREIGN PATENT DOCUMENTS

| DE | 102004031864 A1 * | 1/2006 | ............... G06T 7/11 |
| JP | S62044224 | 2/1987 | |

(Continued)

OTHER PUBLICATIONS

Google Translation of DE102004031864A1 (Year: 2006).*

(Continued)

*Primary Examiner* — Soo Shin
(74) *Attorney, Agent, or Firm* — JCIPRNET

(57) ABSTRACT

A medical image processing apparatus, having a processor configured to divide brains included in a brain image and a standard brain image into a plurality of regions corresponding to each other, calculate a first correction amount between the pixel value of a first reference pixel included in each of the plurality of region in the brain image and the pixel value of a second reference pixel and a second correction amount for matching first other pixel values other than the first reference pixel included in each of the plurality of regions in the brain image with pixel values of second other pixels, and correct the brain image based on the first correction amount and the second correction amount.

20 Claims, 6 Drawing Sheets

(51) Int. Cl.
   *A61B 6/03*   (2006.01)
   *G06T 5/00*   (2006.01)
   *G06T 5/40*   (2006.01)
   *G06T 5/50*   (2006.01)
   *G06T 7/11*   (2017.01)

(52) U.S. Cl.
   CPC ............... *A61B 2576/026* (2013.01); *G06T 2207/10088* (2013.01); *G06T 2207/30016* (2013.01)

(56) References Cited

U.S. PATENT DOCUMENTS

| | | | | |
|---|---|---|---|---|
| 2011/0194744 | A1* | 8/2011 | Wang | G16H 50/50 382/131 |
| 2013/0163836 | A1* | 6/2013 | Pau | G06T 7/62 382/128 |
| 2017/0091574 | A1* | 3/2017 | Udupa | A61N 5/1039 |
| 2018/0315188 | A1* | 11/2018 | Tegzes | G06K 9/2054 |
| 2020/0175662 | A1* | 6/2020 | Wang | G06T 5/008 |

FOREIGN PATENT DOCUMENTS

| | | |
|---|---|---|
| JP | 2001092948 | 4/2001 |
| JP | 2003065969 | 3/2003 |
| JP | 2005237441 | 9/2005 |
| JP | 2007068852 | 3/2007 |
| JP | 2008099889 | 5/2008 |
| JP | 2011010828 | 1/2011 |
| JP | 2011092438 | 5/2011 |
| JP | 2013215471 | 10/2013 |
| JP | 2014042684 | 3/2014 |

OTHER PUBLICATIONS

Zhou et al., "Atlas-Based Fuzzy Connectedness Segmentation and Intensity Nonuniformity Correction Applied to Brain MRI," IEEE Transactions on Biomedical Engineering, vol. 54, No. 1, Jan. 2007 (Year: 2007).*

Jenkinson et al., "Improved Optimization for the Robust and Accurate Linear Registration and Motion Correction of Brain Images," NeuroImage 17, 825-841 (2002) (Year: 2002).*

Abbasi et al., "Detection of brain tumor in 3D MRI images using local binary patterns and histogram orientation gradient," Neurocomputing 219 (2017) 526-535 (Year: 2017).*

Dominic Holland, et al., "Subregional neuroanatomical change as a biomarker for Alzheimer's disease." Proceedings of the National Academy of Sciences, vol. 106, No. 49, Dec. 8, 2009, p. 20954-20959.

Yakang Dai, et al., "aBEAT: A Toolbox for Consistent Analysis of Longitudinal Adult Brain MRI." Plos One, vol. 8, No. 4, Apr. 3, 2013, pp. 1-13.

"International Search Report (Form PCT/ISA/210)"of PCT/JP2018/020700, dated Aug. 21, 2018, with English translation thereof, pp. 1-7.

"Written Opinion of the International Searching Authority (Form PCT/ISA/237)" of PCT/JP2018/020700, dated Aug. 21, 2018, with English translation thereof, pp. 1-9.

"Office Action of Japan Counterpart Application", dated Oct. 6, 2020, with English translation thereof, pp. 1-5.

* cited by examiner

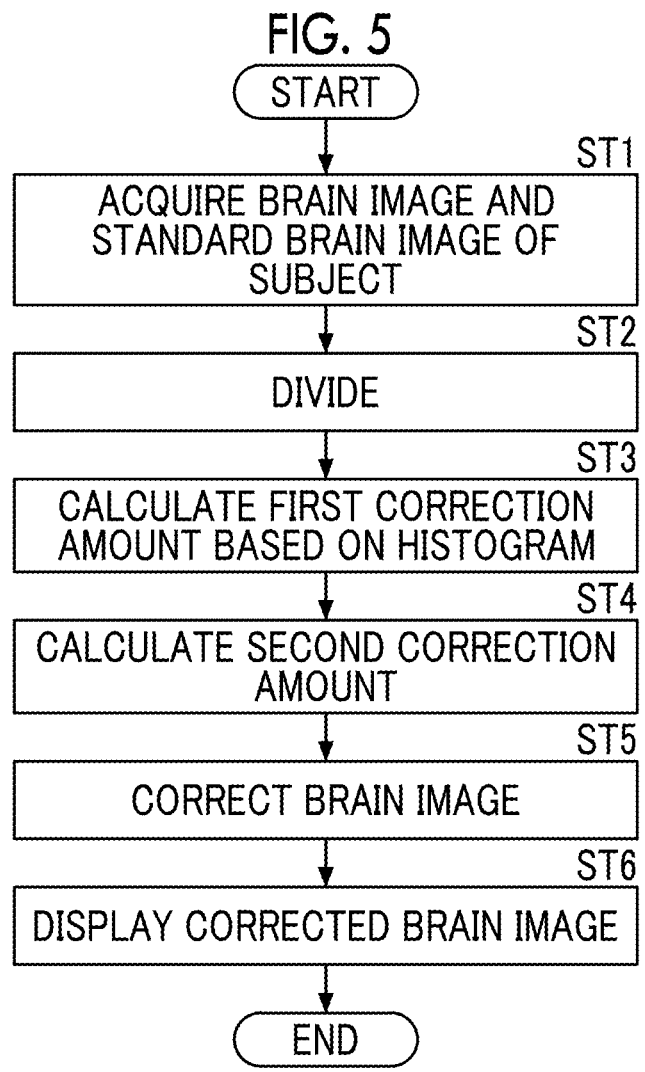

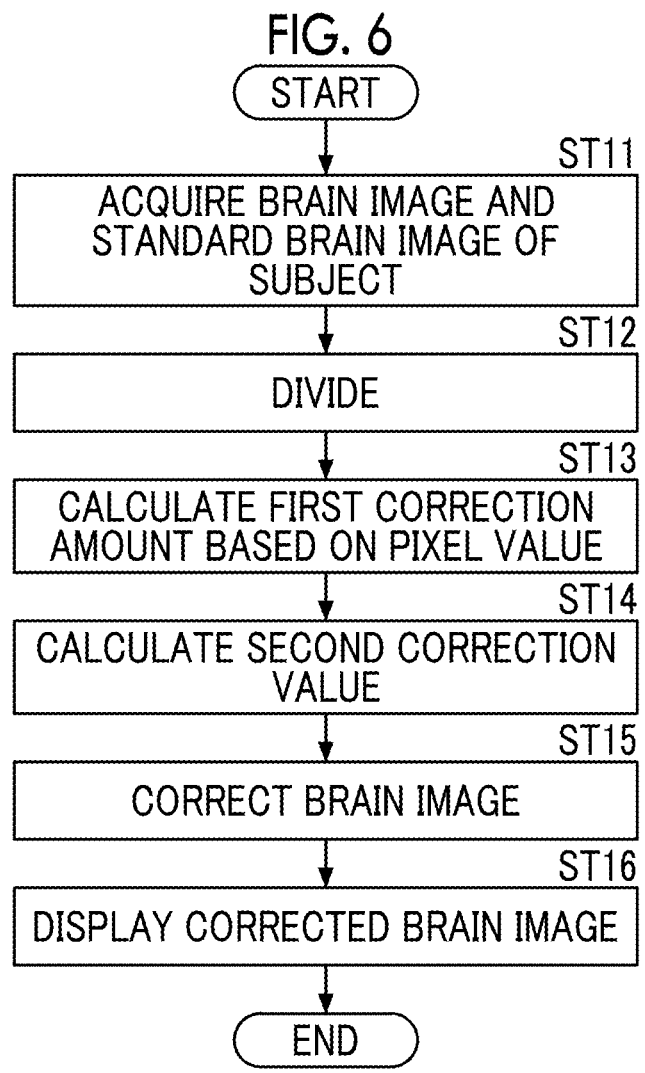

MEDICAL IMAGE PROCESSING APPARATUS, MEDICAL IMAGE PROCESSING METHOD, AND MEDICAL IMAGE PROCESSING PROGRAM

CROSS-REFERENCE TO RELATED APPLICATIONS

This application is a Continuation of PCT International Application No. PCT/JP2018/020700 filed on May 30, 2018, which claims priority under 35 U.S.C. § 119(a) to Japanese Patent Application No. 2017-163010 filed on Aug. 28, 2017. Each of the above application(s) is hereby expressly incorporated by reference, in its entirety, into the present application.

BACKGROUND OF THE INVENTION

1. Field of the Invention

The present invention relates to a medical image processing apparatus, a medical image processing method, and a non-transitory computer readable medium for storing a medical image processing program for correcting the density of a medical image.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, JP2014-042684A has proposed a method of performing registration between two brain images having different imaging dates and times and then dividing each of the two brain images into tissue regions (gray matter and white matter) and acquiring the amount of change for each tissue region.

In addition, for example, a method of performing registration between a brain image of a patient and a standard brain image region-divided according to the Broadmann's brain map and dividing the brain image of the patient into regions has been proposed (refer to JP2011-010828A). Here, the Broadmann's brain map shows which region in the three-dimensional region of the cerebral cortex of the standard brain controls which brain function (motion, language, perception, memory, vision, hearing, and the like). A method has been proposed in which a brain image of a patient is divided into regions and then the amount of change in the volume for each region is acquired (Subregional neuroanatomical change as a biomarker for Alzheimer's disease, Dominic Holland et al., Proceedings of the National Academy of Sciences, Vol. 106, No. 49, pp. 20954-20959, 2009 Dec. 8 and aBEAT: A Toolbox for Consistent Analysis of Longitudinal Adult Brain MRI, Yakang Dai et al., Alzheimer's Disease Neuroimaging Initiative, Apr. 3, 2013). In the methods described in Subregional neuroanatomical change as a biomarker for Alzheimer's disease, Dominic Holland et al., Proceedings of the National Academy of Sciences, Vol. 106, No. 49, pp. 20954-20959, 2009 Dec. 8 and aBEAT: A Toolbox for Consistent Analysis of Longitudinal Adult Brain MRI, Yakang Dai et al., Alzheimer's Disease Neuroimaging Initiative, Apr. 3, 2013, registration between the first brain image of the patient and the standard brain image is performed to divide the first brain image into regions, and registration between the second brain image of the patient, which has a later imaging date and time than the first brain image, and the standard brain image is performed to divide the second brain image into regions. Then, the amount of change in the volume between corresponding regions in the first brain image and the second brain image is acquired.

However, the MRI image acquired by the MRI apparatus has density unevenness due to the apparatus, which is caused by non-uniformity in the static magnetic field and imperfection in the gradient magnetic field. Such density unevenness is not only different depending on the apparatus, but may also occur between two images captured by the same apparatus under the same imaging conditions. Such density unevenness is allowed to some extent. However, in a case where density unevenness is included in two MRI images having different imaging timings for performing follow-up on the same subject, there is a risk that the progress cannot be accurately determined.

In particular, in a case where the subject is a patient with Alzheimer's disease, the atrophy rate of the entire brain is 1 to 3% per year, whereas the atrophy rate of the entire brain of a normal person is less than 1% per year. For this reason, in the follow-up of Alzheimer's disease, it is necessary to compare the MRI image acquired at the time of the previous diagnosis with the latest MRI image to accurately recognize which part of the brain atrophies to which extent. However, in a case where density unevenness is included in the MRI image, there is a possibility that the calculated atrophy of the brain cannot be calculated accurately due to the density unevenness.

For this reason, a method has been proposed in which histograms of two MRI images are calculated and the two histograms are matched to match the densities of the two MRI images with each other (refer to JP2011-92438A).

SUMMARY OF THE INVENTION

By using the method described in JP2011-92438A, it is possible to match the overall densities of the two MRI images with each other. However, it is not possible to correct density unevenness occurring in the images. In addition, density unevenness may occur not only in MRI images but also in CT images and the like.

The present invention has been made in view of the above circumstances, and it is an object of the present invention to make it possible to match the overall densities of two medical images and to correct density unevenness.

A medical image processing apparatus according to the present invention comprises: an image acquisition unit that acquires a first medical image including a target part and a second medical image including the target part; a division unit that divides the target parts included in the first medical image and the second medical image into a plurality of regions corresponding to each other; a first correction amount calculation unit that calculates a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel corresponding to the first reference pixel for each of the plurality of regions in the second medical image; a second correction amount calculation unit that calculates a second correction amount for matching first other pixel values other than the first reference pixel included in each of the plurality of regions in the first medical image with pixel values of second other pixels corresponding to the first other pixels for each of the plurality of regions in the second medical image, based on the first correction amount; and a correction unit that corrects at least one of the first medical image or the second medical image based on the first correction amount and the second correction amount.

The number of "first reference pixels" and the number of "second reference pixels" may be one or plural.

The plurality of regions in the first and second medical images have different pixel values, that is, density values for respective pixels. "Matching the density characteristics of each of the plurality of regions in the first medical image with the density characteristics of the corresponding region in the second medical image" means that the densities of two corresponding regions are made to be the same or similar using, for example, a histogram analysis and a method of analysis using statistical values such as an average value and a variance value of pixels, which will be described later, or a known method.

In the medical image processing apparatus according to the present invention, the first correction amount calculation unit may generate a first histogram in each of the plurality of regions of the first medical image and a second histogram in each of the plurality of regions of the second medical image and calculate, as the first correction amount, a conversion parameter for matching the first histogram in each of the plurality of regions of the first medical image with the second histogram in each of the plurality of regions of the second medical image.

In the medical image processing apparatus according to the present invention, the second correction amount calculation unit may calculate the second correction amount by an interpolation operation for the first correction amount between the plurality of regions. In this case, the interpolation operation may be a linear interpolation operation.

In the medical image processing apparatus according to the present invention, the first medical image and the second medical image may be MRI images.

In the medical image processing apparatus according to the present invention, the target part may be a brain, the first medical image may be a standard brain image, and the second medical image may be a brain image of a subject. The correction unit may correct the brain image of the subject.

In the medical image processing apparatus according to the present invention, the target part may be a brain, and the first medical image and the second medical image may be brain images of the same subject having different imaging times.

In the medical image processing apparatus according to the present invention, the division unit may divide the target part included in each of the first medical image and the second medical image into equal regions.

"Dividing into equal region" includes not only dividing into completely equal regions but also dividing into equal regions with some errors.

A medical image processing method according to the present invention comprises: acquiring a first medical image including a target part and a second medical image including the target part; dividing the target parts included in the first medical image and the second medical image into a plurality of regions corresponding to each other; calculating a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel corresponding to the first reference pixel for each of the plurality of regions in the second medical image; calculating a second correction amount for matching first other pixel values other than the first reference pixel included in each of the plurality of regions in the first medical image with pixel values of second other pixels corresponding to the first other pixels for each of the plurality of regions in the second medical image, based on the first correction amount; and correcting at least one of the first medical image or the second medical image based on the first correction amount and the second correction amount.

In addition, a program causing a computer to execute the medical image processing method according to the present invention may be provided.

Another medical image processing apparatus according to the present invention comprises: a memory that stores commands to be executed by a computer; and a processor configured to execute the stored commands. The processor executes processing for acquiring a first medical image including a target part and a second medical image including the target part; dividing the target parts included in the first medical image and the second medical image into a plurality of regions corresponding to each other; calculating a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel corresponding to the first reference pixel for each of the plurality of regions in the second medical image; calculating a second correction amount for matching first other pixel values other than the first reference pixel included in each of the plurality of regions in the first medical image with pixel values of second other pixels corresponding to the first other pixels for each of the plurality of regions in the second medical image, based on the first correction amount; and correcting at least one of the first medical image or the second medical image based on the first correction amount and the second correction amount.

According to the present invention, the target parts included in the first medical image and the second medical image are divided into a plurality of regions corresponding to each other, and the correction amount for matching the density characteristics of each of the plurality of regions in the first medical image with density characteristics of corresponding regions in the second medical image is calculated as the first correction amount between the pixel value of the first reference pixel included in each of the plurality of regions in the first medical image and the pixel value of the second reference pixel corresponding to the first reference pixel for each of the plurality of regions in the second medical image. Then, the second correction amount for matching the first other pixel values other than the first reference pixel included in each of the plurality of regions in the first medical image with the pixel values of the second other pixels corresponding to the first other pixels for each of the plurality of regions in the second medical image is calculated based on the first correction amount. In addition, at least one of the first medical image or the second medical image is corrected based on the first correction amount and the second correction amount. For this reason, even in a case where the first medical image and the second medical image include unevenness of different pixel values, that is, density unevenness, not only the overall densities of the first medical image and the second medical image but also the density unevenness of the first medical image and the density unevenness of the second medical image can be matched with each other. Therefore, by using the corrected first medical image and second medical image, it is possible to accurately compare the target parts included in the first medical image and the second medical image with each other.

BRIEF DESCRIPTION OF THE DRAWINGS

FIG. 5 is a flowchart showing the process performed in a first embodiment.

FIG. 6 is a flowchart showing the process performed in a second embodiment.

DESCRIPTION OF THE PREFERRED EMBODIMENTS

Figure 1:
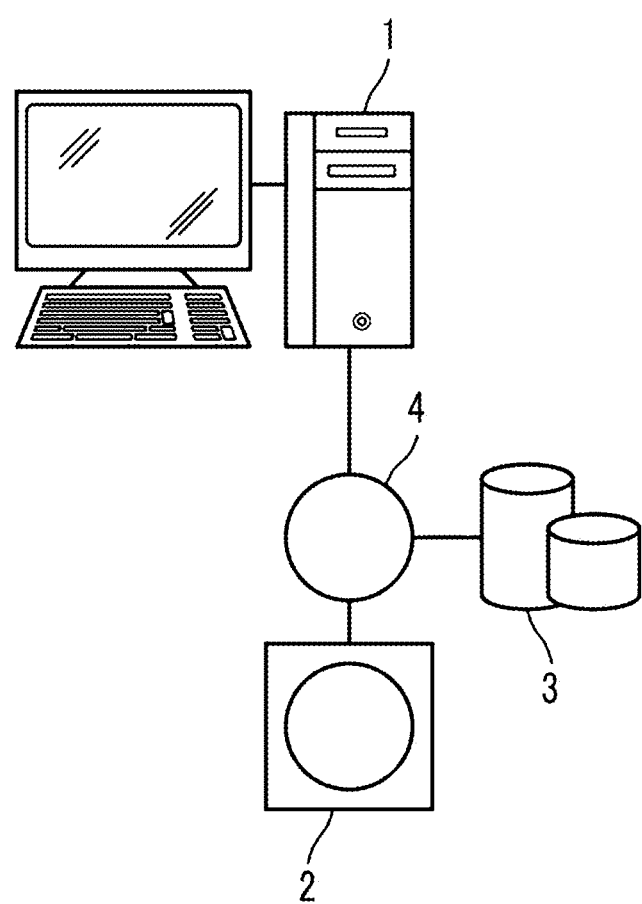
FIG. 1 is a hardware configuration diagram showing an outline of a diagnostic support system to which a medical image processing apparatus according to an embodiment of the present invention is applied.

Hereinafter, embodiments of the present invention will be described with reference to the accompanying diagrams. FIG. 1 is a hardware configuration diagram showing the outline of a diagnostic support system to which a medical image processing apparatus according to an embodiment of the present invention is applied. As shown in FIG. 1, in the diagnostic support system, a medical image processing apparatus 1 according to the present embodiment, a three-dimensional image capturing apparatus 2, and an image storage server 3 are communicably connected to each other through a network 4.

The three-dimensional image capturing apparatus 2 is an apparatus that generates a three-dimensional image showing a part, which is a diagnostic target part of a patient who is a subject, as a medical image by imaging the part. Specifically, the three-dimensional image capturing apparatus 2 is a CT apparatus, an MRI apparatus, a PET apparatus, or the like. The medical image generated by the three-dimensional image capturing apparatus 2 is transmitted to the image storage server 3 and is stored therein. In the present embodiment, a diagnostic target part of a patient who is a subject is a brain, the three-dimensional image capturing apparatus 2 is an MRI apparatus, and an MRI image of the head including the brain of the subject is generated as a three-dimensional medical image.

The image storage server 3 is a computer that stores and manages various kinds of data, and comprises a large-capacity external storage device and software for database management. The image storage server 3 communicates with other apparatuses through the wired or wireless network 4 to transmit and receive image data or the like. Specifically, the image storage server 3 acquires various kinds of data including image data of the medical image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DI-COM). In the present embodiment, it is assumed that a plurality of three-dimensional medical images having different imaging dates and times for the same subject are stored in the image storage server 3. In addition, it is assumed that image data of a standard brain image to be described later is also stored in the image storage server 3.

The medical image processing apparatus 1 is realized by installing a medical image processing program of the present invention on one computer. The computer may be a workstation or a personal computer that is directly operated by a doctor who performs diagnosis, or may be a server computer connected to these through a network. The medical image processing program is distributed in a state in which the medical image processing program is recorded on a recording medium, such as a digital versatile disc (DVD) or a compact disc read only memory (CD-ROM), and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
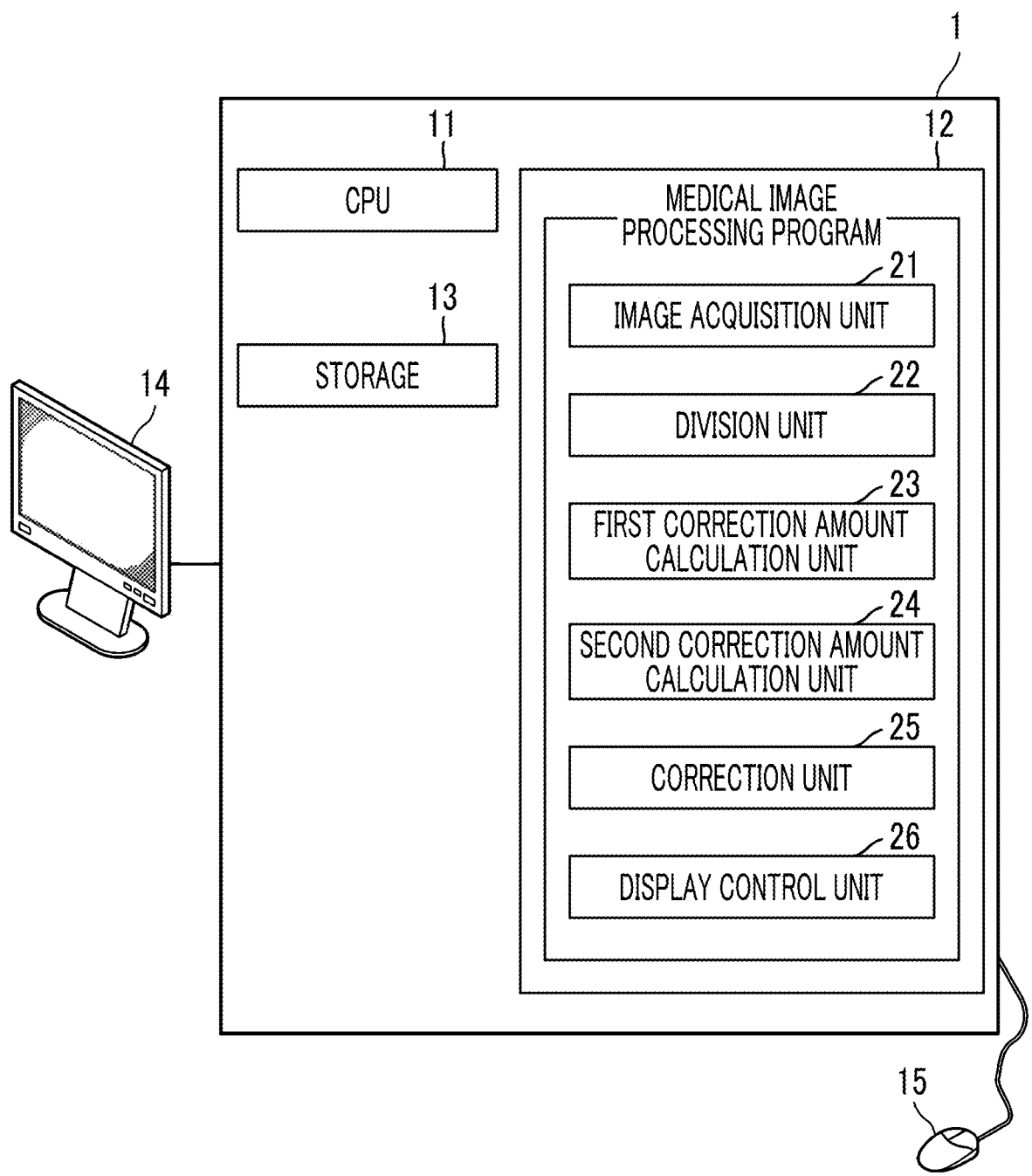
FIG. 2 is a diagram showing the schematic configuration of the medical image processing apparatus.

FIG. 2 is a diagram showing the schematic configuration of a medical image processing apparatus realized by installing a medical image processing program on a computer. As shown in FIG. 2, the medical image processing apparatus 1 comprises a central processing unit (CPU) 11, a memory 12, and a storage 13 as the configuration of a standard workstation. A display 14, such as a liquid crystal display, and an input unit 15, such as a keyboard and a mouse, are connected to the medical image processing apparatus 1.

The storage 13 is a storage device, such as a hard disk or a solid state drive (SSD). A brain image B0 of the subject, a standard brain image Bs, and various kinds of information including information required for processing, which are acquired from the image storage server 3 through the network 4, are stored in the storage 13. The brain image B0 of the subject corresponds to a first medical image, and the standard brain image Bs corresponds to a second medical image.

Here, the standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains. The standard brain image Bs may be created by computer graphics or the like. Alternatively, a brain image of one healthy person may be used as the standard brain image Bs.

A medical image processing program is stored in the memory 12. As processing to be executed by the CPU 11, the medical image processing program defines: image acquisition processing for acquiring the brain image B0 of the subject and the standard brain image Bs; division processing for dividing the brains included in the brain image B0 and the standard brain image Bs into a plurality of regions corresponding to each other; first correction amount calculation processing for calculating a correction amount for matching the density characteristics of each of the plurality of regions in the brain image B0 with the density characteristics of corresponding regions in the standard brain image Bs as a first correction amount between the pixel value of a first reference pixel included in each of the plurality of regions in the brain image B0 and the pixel value of a second reference pixel corresponding to the first reference pixel for each of the plurality of regions in the standard brain image Bs; second correction amount calculation processing for calculating a second correction amount for matching first other pixel values other than the first reference pixel included in each of the plurality of regions in the brain image B0 with pixel values of second other pixels corresponding to the first other pixels for each of the plurality of regions in the standard brain image Bs, based on the first correction amount; correction processing for correcting the brain image B0 based on the first correction amount and the second correction amount; and display control processing for displaying the corrected brain image B0 on the display 14.

The CPU 11 executes these processes according to the program, so that the computer functions as an image acquisition unit 21, a division unit 22, a first correction amount calculation unit 23, a second correction amount calculation unit 24, a correction unit 25, and a display control unit 26. The medical image processing apparatus 1 may comprise a plurality of processors or processing circuits that perform image acquisition processing, division processing, first correction amount calculation processing, second correction amount calculation processing, correction processing, and display control processing.

The image acquisition unit 21 acquires the brain image B0 of the subject and the standard brain image Bs from the image storage server 3. In a case where the brain image B0 and the standard brain image Bs are already stored in the storage 13, the image acquisition unit 21 may acquire the brain image B0 and the standard brain image Bs from the storage 13. In the present embodiment, those stored in the image storage server 3 are the brain images B0 acquired by imaging the head of the subject, and include structures other than the brain, such as a skull.

Figure 3:
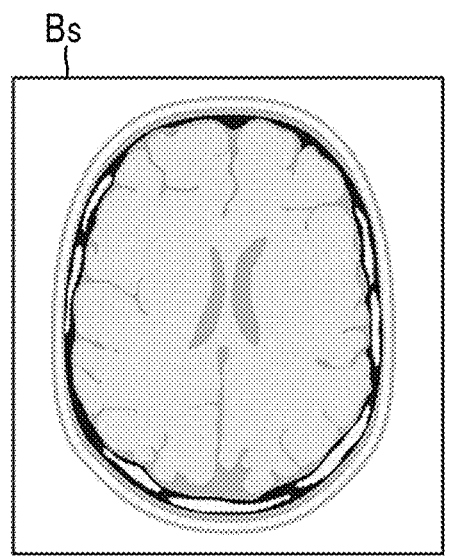
FIG. 3 is a diagram illustrating the division of a standard brain image.
Figure 3:
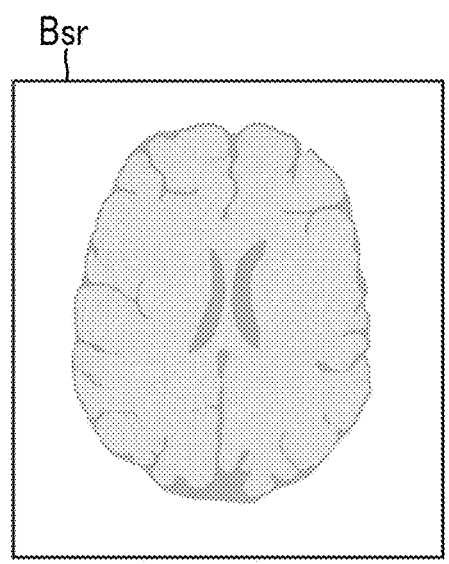
Figure 3:
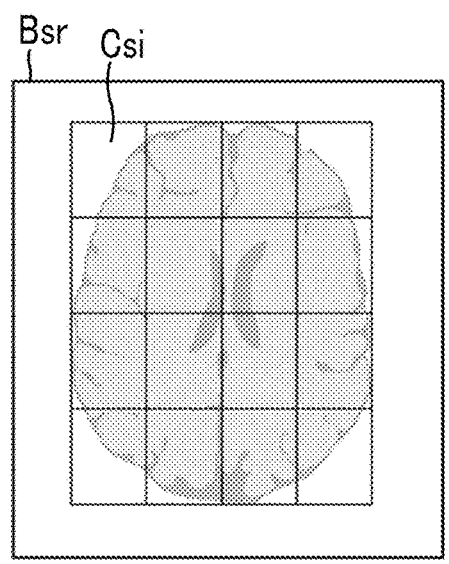

The division unit 22 divides the brains included in the brain image B0 and the standard brain image Bs into a plurality of regions corresponding to each other. First, the division of the standard brain image Bs will be described. FIG. 3 is a diagram illustrating the division of a standard brain image. The standard brain image Bs is a three-dimensional image, but FIG. 3 shows a slice image of one axial section in the standard brain image Bs. Here, in the present embodiment, brain regions are extracted in advance for the standard brain image Bs. For this reason, the division unit 22 generates a standard brain region image Bsr in which only the brain region in the standard brain image Bs is extracted. Then, the division unit 22 divides the standard brain region image Bsr into a plurality of small regions. The small region corresponds to a region of the present invention.

In the present embodiment, since the standard brain region image Bsr is a three-dimensional image, the standard brain region image Bsr is equally divided into four regions in each of the three directions of x, y, and z, and the standard brain region image Bsr is divided into 64 small regions $Csi$ (i=1 to 64) in each of the three directions of x, y, and z. In this case, the boundaries of the small regions may be adjusted so that the volumes of the small regions $Csi$ are the same. The number of divisions of the region is not limited to 64, and may be any number. In the above description, the standard brain region image Bsr is equally divided, but may be unequally divided. By dividing the standard brain region image Bsr equally into four regions in each of the three directions of x, y, and z, each small region $Csi$ has a cubic shape. However, the standard brain region image Bsr may be divided so that each small region $Csi$ has a rectangular parallelepiped shape, or may be divided so that each small region $Csi$ has any three-dimensional shape.

Figure 4:
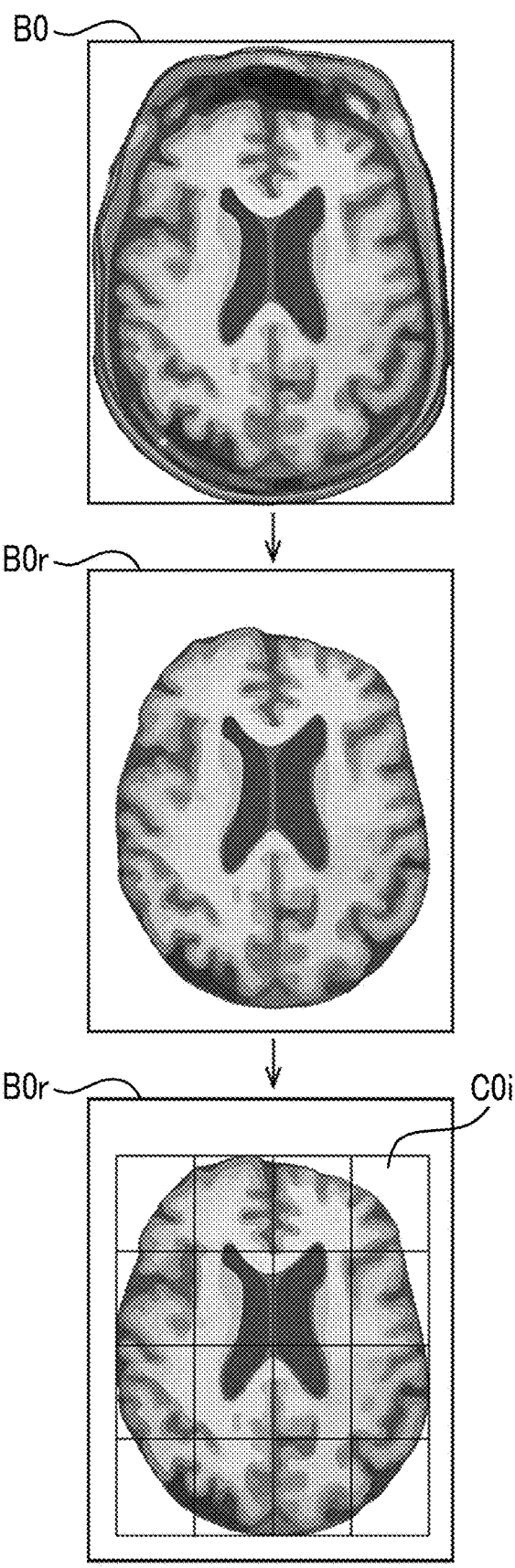
FIG. 4 is a diagram illustrating the division of a brain image.

The division unit 22 divides the brain region of the brain image B0 in the same manner as the standard brain image Bs. FIG. 4 is a diagram illustrating the division of a brain image. In order to divide the brain image B0, the division unit 22 registrates the brain image B0 with the standard brain image Bs. In the present embodiment, the following description will be given on the assumption that the standard brain image Bs is registered with the brain image B0. However, the brain image B0 may be registered with the standard brain image Bs.

For registration, the division unit 22 extracts landmarks from the brain image B0 and the standard brain image Bs. For example, landmarks may be extracted by template matching using a template indicating a landmark, or may be extracted using a discriminator that has been learned to discriminate landmarks included in an image. The division unit 22 performs the first registration between the brain image B0 and the standard brain image Bs so that the corresponding landmarks match each other. In the present embodiment, the first registration is registration by similarity transformation. Specifically, the first registration is registration by parallel movement, rotation, and similar enlargement and reduction of the standard brain image Bs. The division unit 22 performs the first registration by performing similarity transformation of the standard brain image Bs so that the correlation between the landmark included in the standard brain image Bs and the corresponding landmark included in the brain image B0 is maximized.

After performing the first registration using the landmarks as described above, the division unit 22 performs the second registration using the entire region between the brain image B0 and the standard brain image Bs. In the present embodiment, the second registration is registration by nonlinear transformation. As the registration by nonlinear transformation, for example, there is registration performed by nonlinearly converting pixel positions using functions, such as B spline and thin plate spline. The division unit 22 performs the second registration by nonlinearly converting each pixel position of the standard brain image Bs after the first registration to a corresponding pixel position included in the brain image B0.

After registrating the standard brain image Bs with the brain image B0 as described above, the division unit 22 generates a brain region image B0r by extracting the brain region from the brain image B0 by applying the brain region of the standard brain image Bs to the brain image B0. For the extracted brain region, a brain region may be more accurately extracted from the brain image B0 using, for example, a graph cutting method or the like.

Then, the division unit 22 divides the brain region image B0r into a plurality of regions in the same manner as the standard brain region image Bsr. In the present embodiment, the standard brain region image Bsr is divided into 64 small regions Csi. Therefore, the division unit 22 divides the brain region image B0r into 64 small regions C0i (i=1 to 64). In this case, the boundaries of the small regions may be adjusted so that the volumes of the small regions C0i are the same.

The first correction amount calculation unit 23 calculates a correction amount for matching the density characteristics of each of the plurality of small regions C0i in the brain image B0 with the density characteristics of the corresponding small region Csi in the standard brain image Bs as a first correction amount between the pixel value of a first reference pixel included in each of the plurality of small regions C0i in the brain image B0 and the pixel value of a second reference pixel corresponding to the first reference pixel for each of the plurality of small regions Csi in the standard brain image Bs. In the present embodiment, it is assumed that the density characteristics of each of the plurality of small regions C0i in the brain image B0 are matched with the density characteristics of the corresponding small region Csi in the standard brain image Bs. In the present embodiment, the first reference pixel is the central pixel of the small region C0i, and the second reference pixel is the central pixel of the small region Cri. However, the present invention is not limited thereto.

First, the first correction amount calculation unit 23 generates a histogram H0i of a pixel value for each of the plurality of small regions C0i in the brain image B0 and a histogram Hsi of a pixel value for each of the plurality of small regions Csi in the standard brain image Bs. Then, a conversion parameter for matching the histogram H0i and the histogram Hsi between the small region C0i and the small region Csi corresponding to each other is calculated as the first correction amount. Specifically, the first correction amount calculation unit 23 calculates the first correction amount so that each of the minimum value and the maximum value of the histogram H0i in the brain image B0 match the minimum value and the maximum value of the histogram Hsi in the standard brain image Bs.

Here, it is assumed that the minimum value and the maximum value of the pixel value in the histogram H0i of the brain image B0 are S0min(i) and S0max(i), respectively, and the minimum value and the maximum value of the pixel value in the histogram Hsi of the standard brain image Bs are Ssmin(i) and Srmax(i), respectively. In addition, it is assumed that any pixel value in the histogram H0i is S0(i) and the pixel value S0(i) corrected with the first correction amount is Sc0(i). In this case, the relationship shown in the following Equation (1) is established.

$$Sc0(i)=Ssmin(i)+(S0(i)-S0min(i))*(Ssmax(i)-Ssmin(i))/(S0max(i)-S0min(i)) \quad (1)$$

Equation (1) is a linear transformation and can be expressed by two transformation parameters a(i) and b(i), and therefore Equation (1) can be transformed into the following Equation (2).

$$Sc0(i)=a(i)*S0(i)+b(i) \quad (2)$$

Here, $a(i)=(Ssmax(i)-Ssmin(i))/(S0max(i)-S0min(i))$
$b(i)=Ssmin(i)-S0min(i)*(Ssmax(i)-Ssmin(i))/(S0max(i)-S0min(i))$ For each of the small regions C0i, the first correction amount calculation unit 23 calculates the conversion parameters a(i) and b(i) in the above Equation (2) as the first correction amount between the pixel value of the first reference pixel (that is, the central pixel of the small region C0i) and the pixel value of the second reference pixel (that is, the central pixel of the small region Csi).

Here, by correcting all the pixels in the small region C0i with the first correction amount calculated as described above, the density characteristics of the small region C0i can be made to match the density characteristics of the corresponding small region Csi in the standard brain image Bs. However, since the first correction amount is calculated for each of the small regions C0i, a density difference appears at the boundary of the small regions C0i in a case where all the pixels in each small region C0i are corrected with the first correction amount.

For this reason, the second correction amount calculation unit 24 calculates a second correction amount for matching first other pixel values other than the first reference pixel included in each of the plurality of small regions C0i in the brain image B0 with the pixel values of second other pixels corresponding to the first other pixels for each of the plurality of small regions Csi in the standard brain image Bs, based on the first correction amount. In the present embodiment, it is assumed that the pixel values of the first other pixels in the brain image B0 are matched with the pixel value of another second pixel in the standard brain image Bs. In the present embodiment, since the first reference pixel is the central pixel of the small region C0i and the second reference pixel is the central pixel of the small region Cri, the first other pixels are all pixels other than the central pixel in the small region C0i and the second other pixels are all pixels other than the central pixel corresponding to the first other pixels in the small region Cri.

The first correction amount calculated by the first correction amount calculation unit 23 is the conversion parameters a(i) and b(i) for converting the pixel value of the first reference pixel (that is, the central pixel of the small region C0i) into the pixel value of the second reference pixel (that is, the small region Csi). Here, a small region adjacent to the small region C0i to be corrected is set to Ckj (j is the number of small regions). The number j of small regions differs depending on the location of the small region in the brain image B0, and the minimum is 7 and the maximum is 26. The second correction amount calculation unit 24 linearly interpolates the conversion parameters a(i) and b(i) of the target small region C0i and conversion parameters ak(j) and bk(j) of a plurality of small regions Ckj adjacent to the target small region C0i, and calculates conversion parameters ah(i) and bh(i) for first other pixels other than the first reference pixel of the target small region C0i as the second correction amount.

In addition, for the first other pixels between the central pixel in the small region C0i and the central pixel in the small region Ckj adjacent to the small region C0i, the second correction amount can be calculated by the linear interpolation described above. On the other hand, in the small region C0i at the boundary between the brain and the background in the brain image B0, the second correction amount may not be calculated by the above-described linear interpolation depending on the positions of the first other pixels. The conversion parameters ah(i) and bh(i) for the first other pixels may be calculated by extrapolation using the conversion parameters ak(j) and bk(j) of the adjacent small region Ckj.

The correction unit 25 corrects the brain image B0 based on the first correction amount and the second correction amount. That is, in each of the small regions C0$i$ of the brain image B0, for the first reference pixel, the pixel value is corrected by the conversion parameters a(i) and b(i) that are the first correction amounts. On the other hand, for the first other pixels, the pixel values are corrected by the conversion parameters ah(i) and bh(i) that re the second correction amounts. In this manner, the correction unit 25 generates a corrected brain image Bf0.

The display control unit 26 displays the corrected brain image Bf0 on the display 14.

Next, the operation of the first embodiment will be described. FIG. 5 is a flowchart showing the process performed in the first embodiment. First, the image acquisition unit 21 acquires the brain image B0 and the standard brain image Bs of the subject (step ST1), and the division unit 22 divides the brains included in the brain image B0 and the standard brain image Bs into a plurality of small regions C0$i$ and a plurality of small regions Cs$i$ corresponding to each other (step ST2). Then, the first correction amount calculation unit 23 calculates a first correction amount between the pixel value of the first reference pixel included in each of the plurality of small region C0$i$ in the brain image B0 and the pixel value of the second reference pixel corresponding to the first reference pixel for each of the plurality of small regions Cs$i$ in the standard brain image Bs based on the histograms of the small region C0$i$ and the small region Cs$i$ (step ST3).

In addition, the second correction amount calculation unit 24 calculates a second correction amount for matching the first other pixel values other than the first reference pixel included in each of the plurality of small regions C0$i$ in the brain image B0 with the pixel values of the second other pixels corresponding to the first other pixels for each of the plurality of small regions Cs$i$ in the standard brain image Bs (step ST4). Then, the correction unit 25 corrects the brain image B0 based on the first correction amount and the second correction amount (step ST5), the display control unit 26 displays the corrected brain image Bf0 on the display 14 (step ST6), and the process ends.

As described above, in the present embodiment, the brains included in the brain image B0 and the standard brain image Bs are respectively divided into a plurality of small regions C0$i$ and a plurality of small regions Cs$i$, the correction amount for matching the density characteristics of each of the plurality of small regions C0$i$ in the brain image B0 with the density characteristics of the corresponding small region Cs$i$ in the standard brain image Bs is calculated as the first correction amount between the pixel value of the first reference pixel of the small region C0$i$ of the brain image B0 and the pixel value of the second reference pixel of the small region Cs$i$ of the standard brain image Bs, and the second correction amount for matching the first other pixel values other than the first reference pixel of the small region C0$i$ of the brain image B0 with the pixel values of the second other pixels corresponding to the first other pixels of the small region Cs$i$ of the standard brain image Bs is calculated based on the first correction amount. Then, the brain image B0 is corrected based on the first correction amount and the second correction amount. For this reason, even in a case where the brain image B0 includes unevenness of different pixel values, that is, density unevenness, the density of the brain image B0 can be matched with the density of the standard brain image Bs including not only the overall density of the brain image B0 but also the density unevenness. Therefore, by using the corrected brain image B0, it is possible to accurately compare the brain image B0 and the standard brain image Bs with each other.

In addition, by calculating the second correction amount by the interpolation operation for the first correction amount between the plurality of small regions C0$i$, the boundary of the small regions C0$i$ can be made not to be noticeable in the corrected brain image Bf0. In particular, by performing a linear interpolation operation as the interpolation operation, the boundary of the small regions C0$i$ can be made less noticeable in the corrected brain image Bf0.

By using an MRI image as the brain image B0, it is possible to correct density unevenness due to the apparatus, which is included in the MRI image due to non-uniformity in the static magnetic field and imperfection in the gradient magnetic field.

Next, a second embodiment of the present invention will be described. The configuration of a medical image processing apparatus according to the second embodiment is the same as the configuration of the medical image processing apparatus according to the first embodiment shown in FIG. 2, and only the processing to be performed is different. Accordingly, the detailed description of the apparatus will be omitted herein. In the first embodiment described above, the first correction amount calculation unit 23 calculates the first correction amount using the histograms of the small region C0$i$ and the small region Cs$i$. The second embodiment is different from the first embodiment in that the first correction amount is calculated using the pixel values of the small region C0$i$ and the small region Cs$i$, specifically, the average value and the variance value of the pixel values, without using a histogram.

In the second embodiment, the first correction amount calculation unit 23 calculates an average value Ms$i$ and a variance value Vs$i$ of the pixel values in the small region Cs$i$ for each of the small regions Cs$i$ of the standard brain image Bs. For each small region C0$i$ of the brain image B0, an average value M0$i$ and a variance value V0$i$ of the pixel values in the small region C0$i$ are calculated. The average value and the variance value are representative values of the pixel value, but may be an intermediate value or the like.

Then, the first correction amount calculation unit 23 calculates the first correction amount so that the average value M0$i$ and the variance value V0$i$ match the average value Ms$i$ and the variance value Vs$i$, respectively, between the small region C0$i$ and the small region Cs$i$ corresponding to each other. Here, assuming that the pixel value S0(i) after correction using the first correction amount is Sc0(i), the relationship shown in the following Equation (3) is established.

$$Sc0(i) = Msi + (S0(i) - M0i) * Vsi/V0i \quad (3)$$

Equation (3) is a linear transformation and can be expressed by two transformation parameters e(i) and f(i), and therefore Equation (3) can be transformed into the following Equation (4).

$$Sc0(i) = e(i) * S0(i) + f(i) \quad (4)$$

Here, e(i)=Vs$i$/V0$i$
f(i)=Ms$i$−M0$i$*Vs$i$/V0$i$

For each of the small regions C0$i$, the first correction amount calculation unit 23 calculates the conversion parameters e(i) and f(i) in the above Equation (4) as the first correction amount between the pixel value of the first reference pixel (that is, the central pixel of the small region C0$i$) and the pixel value of the second reference pixel (that is, the central pixel of the small region Cs$i$).

In the second embodiment, the processing performed by the second correction amount calculation unit 24 is the same as that in the first embodiment except that the first correction amount is the conversion parameters e(i) and f(i). That is, the second correction amount calculation unit 24 linearly interpolates the conversion parameters e(i) and f(i) of the target small region C0$i$ and conversion parameters ck(j) and dk(j) of a plurality of small regions Ckj adjacent to the target small region C0$i$, and calculates conversion parameters eh(i) and fh(i) for first other pixels other than the first reference pixel of the target small region C0$i$ as the second correction amount.

Next, the operation of the second embodiment will be described. FIG. 6 is a flowchart showing the process performed in the second embodiment. First, the image acquisition unit 21 acquires the brain image B0 and the standard brain image Bs of the subject (step ST11), and the division unit 22 divides the brains included in the brain image B0 and the standard brain image Bs into a plurality of small regions C0$i$ and a plurality of small regions Csi corresponding to each other (step ST12). Then, the first correction amount calculation unit 23 calculates a first correction amount between the pixel value of the first reference pixel included in each of the plurality of small region C0$i$ in the brain image B0 and the pixel value of the second reference pixel corresponding to the first reference pixel for each of the plurality of small regions Csi in the standard brain image Bs based on the pixel values of the small region C0$i$ and the small region Csi (step ST13).

In addition, the second correction amount calculation unit 24 calculates a second correction amount for matching the first other pixel values other than the first reference pixel included in each of the plurality of small regions C0$i$ in the brain image B0 with the pixel values of the second other pixels corresponding to the first other pixels for each of the plurality of small regions Csi in the standard brain image Bs (step ST14). Then, the correction unit 25 corrects the brain image B0 based on the first correction amount and the second correction amount (step ST15), the display control unit 26 displays the corrected brain image B0 on the display 14 (step ST16), and the process ends.

In the first and second embodiments described above, the brain image B0 and the standard brain image Bs are acquired, and the brain image B0 is corrected so that the density of the brain image B0 matches the density of the standard brain image Bs. However, the present invention can also be applied to a case where the first brain image and the second brain image having different imaging times for the same subject are acquired and correction is performed so that the density of one of the first brain image and the second brain image matches the density of the other one. In this case, by replacing the first brain image with the brain image B0 and replacing the second brain image with the standard brain image Bs in the first and second embodiments described above, it is possible to correct the first brain image as in the first embodiment.

In the embodiment described above, the MRI image of the subject is used as a medical image. However, brain images other than the MRI image, such as a CT image and a PET image, may be used.

In the embodiments described above, the brain is used as a target part. However, the present invention is not limited thereto, and any anatomical region included in the human body, such as the heart, liver, and lung, can be used as a target part.

Hereinafter, the effect of the present embodiment will be described.

By calculating the second correction amount by the interpolation operation for the first correction amount between a plurality of regions, the boundary of the regions can be made not to be noticeable in at least one of the corrected first medical image or the corrected second medical image.

In particular, by performing a linear interpolation operation as the interpolation operation, the boundary of the regions can be made less noticeable in at least one of the corrected first medical image or the corrected second medical image.

By using MRI images as the first and second medical images, it is possible to correct density unevenness due to the apparatus, which is included in the MRI image due to non-uniformity in the static magnetic field and imperfection in the gradient magnetic field.

By using the brain as a target part, using the first medical image as a standard brain image, using the brain image of the subject as the second medical image, and correcting the brain image of the subject, it is possible to match the density of the brain image of the subject with the density of the standard brain image and to correct density unevenness included in the brain image of the subject. Therefore, it is possible to accurately compare the brain included in the brain image of the subject with the standard brain image.

By using the brain as a target part and using the brain images of the same subject having different imaging timings as the first and second medical images, it is possible to accurately compare the brain images having different imaging timings.

EXPLANATION OF REFERENCES

1: medical image processing apparatus
2: three-dimensional image capturing apparatus
3: image storage server
4: network
11: CPU
12: memory
13: storage
14: display
15: input unit
21: image acquisition unit
22: division unit
23: first correction amount calculation unit
24: second correction amount calculation unit
25: correction unit
26: display control unit
C0$i$, Csi: small region
B0: brain image
B0$r$: brain region image
Bs: standard brain image
Bsr: standard brain region image

What is claimed is:

1. A medical image processing apparatus, comprising a processor configured to:
   acquire a first medical image including an image of a target part and a second medical image including an image of the target part;
   divide the images of the target part included in the first medical image and the second medical image into a plurality of regions corresponding to each other;
   calculate a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel included in each of the plurality of regions in the second medical image corresponding to where the first reference pixel is chosen, wherein the density characteristics of each of the plurality of regions in the first medical image and the second medical image correspond to density values for respective pixels in each of the plurality of regions in the first medical image and in the second medical image;

calculate a second correction amount for matching first other pixel values other than the first reference pixel included in each of the plurality of regions in the first medical image with pixel values of second other pixels included in each of the plurality of regions in the second medical image corresponding to where the first other pixel values are chosen, based on the first correction amount; and correct at least one of the first medical image or the second medical image based on the first correction amount and the second correction amount.

2. The medical image processing apparatus according to claim 1,
wherein the processor configured to:
generate a first histogram in each of the plurality of regions of the first medical image and a second histogram in each of the plurality of regions of the second medical image, wherein the first histogram is constituted by pixel values in the each of the plurality of regions of the first medical image, and the second histogram is constituted by pixel values in the each of the plurality of regions of the second medical image; and
calculate, as the first correction amount, a conversion parameter for matching the first histogram in each of the plurality of regions of the first medical image with the second histogram in each of the plurality of regions of the second medical image.

3. The medical image processing apparatus according to claim 1,
wherein the processor configured to calculate the second correction amount by an interpolation operation for the first correction amount between the plurality of regions.

4. The medical image processing apparatus according to claim 2,
wherein the processor configured to calculate the second correction amount by an interpolation operation for the first correction amount between the plurality of regions.

5. The medical image processing apparatus according to claim 3,
wherein the interpolation operation is a linear interpolation operation.

6. The medical image processing apparatus according to claim 1,
wherein the first medical image and the second medical image are MRI images.

7. The medical image processing apparatus according to claim 2,
wherein the first medical image and the second medical image are MRI images.

8. The medical image processing apparatus according to claim 3,
wherein the first medical image and the second medical image are MRI images.

9. The medical image processing apparatus according to claim 4,
wherein the first medical image and the second medical image are MRI images.

10. The medical image processing apparatus according to claim 5,
wherein the first medical image and the second medical image are MRI images.

11. The medical image processing apparatus according to claim 1,
wherein the target part is a brain, the first medical image is a standard brain image, and the second medical image is a brain image of a subject, and
the processor configured to correct the brain image of the subject.

12. The medical image processing apparatus according to claim 2,
wherein the target part is a brain, the first medical image is a standard brain image, and the second medical image is a brain image of a subject, and
the processor configured to correct the brain image of the subject.

13. The medical image processing apparatus according to claim 3,
wherein the target part is a brain, the first medical image is a standard brain image, and the second medical image is a brain image of a subject, and
the processor configured to correct the brain image of the subject.

14. The medical image processing apparatus according to claim 4,
wherein the target part is a brain, the first medical image is a standard brain image, and the second medical image is a brain image of a subject, and
the processor configured to correct the brain image of the subject.

15. The medical image processing apparatus according to claim 5,
wherein the target part is a brain, the first medical image is a standard brain image, and the second medical image is a brain image of a subject, and
the processor configured to correct the brain image of the subject.

16. The medical image processing apparatus according to claim 6,
wherein the target part is a brain, the first medical image is a standard brain image, and the second medical image is a brain image of a subject, and
the processor configured to correct the brain image of the subject.

17. The medical image processing apparatus according to claim 1,
wherein the target part is a brain, and the first medical image and the second medical image are brain images of the same subject having different imaging times.

18. The medical image processing apparatus according to claim 1,
wherein the division unit divides the image of the target part included in each of the first medical image and the second medical image into equal regions.

19. A medical image processing method, comprising:
acquiring a first medical image including an image of a target part and a second medical image including an image of the target part;
dividing the images of the target part included in the first medical image and the second medical image into a plurality of regions corresponding to each other;
calculating a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel included in each of the plurality of regions in the second medical image corresponding to where the first reference pixel is chosen, wherein the density characteristics of each of the plurality of regions in the first medical image and the second medical image correspond to density values for respective pixels in each of the plurality of regions in the first medical image and in the second medical image;

calculating a second correction amount for matching first other pixel values other than the first reference pixel included in each of the plurality of regions in the first medical image with pixel values of second other pixels included in each of the plurality of regions in the second medical image corresponding to where the first other pixel values are chosen, based on the first correction amount; and correcting at least one of the first medical image or the second medical image based on the first correction amount and the second correction amount.

20. A non-transitory computer readable medium for storing a medical image processing program causing a computer to execute a process comprising:

acquiring a first medical image including an image of a target part and a second medical image including an image of the target part;

dividing the images of the target part included in the first medical image and the second medical image into a plurality of regions corresponding to each other;

calculating a correction amount for matching density characteristics of each of the plurality of regions in the first medical image with density characteristics of corresponding regions in the second medical image as a first correction amount between a pixel value of a first reference pixel included in each of the plurality of regions in the first medical image and a pixel value of a second reference pixel included in each of the plurality of regions in the second medical image corresponding to where the first reference pixel is chosen, wherein the density characteristics of each of the plurality of regions in the first medical image and the second medical image correspond to density values for respective pixels in each of the plurality of regions in the first medical image and in the second medical image;

calculating a second correction amount for matching first other pixel values other than the first reference pixel included in each of the plurality of regions in the first medical image with pixel values of second other pixels included in each of the plurality of regions in the second medical image corresponding to where the first other pixel values are chosen, based on the first correction amount; and correcting at least one of the first medical image or the second medical image based on the first correction amount and the second correction amount.

* * * * *